United States Patent [19]

Lutz et al.

[11] 4,098,812
[45] Jul. 4, 1978

[54] 4-CYANO-2,6-DINITROANILINES

[75] Inventors: Albert William Lutz, Princeton; Robert Eugene Diehl, Lawrenceville, both of N.J.

[73] Assignee: American Cyanamid Company, Stamford, Conn.

[21] Appl. No.: 752,051

[22] Filed: Dec. 20, 1976

Related U.S. Application Data

[60] Continuation-in-part of Ser. No. 705,864, Jul. 16, 1976, abandoned, which is a continuation-in-part of Ser. No. 599,288, Jul. 25, 1975, abandoned, which is a division of Ser. No. 323,000, Jan. 12, 1973, Pat. No. 3,920,742, which is a continuation-in-part of Ser. No. 262,807, Jun. 14, 1972, abandoned, which is a continuation-in-part of Ser. No. 174,938, Aug. 25, 1971, abandoned.

[51] Int. Cl.$^2$ ............................................. C07C 121/78
[52] U.S. Cl. .................................. 260/465 E; 71/105
[58] Field of Search ..................................... 260/465 E

[56] References Cited
U.S. PATENT DOCUMENTS 3,257,190   6/1966   Soper ........................... 260/465 E X Primary Examiner—Dolph H. Torrence
Attorney, Agent, or Firm—H. G. Jackson

[57] ABSTRACT

This invention relates to certain novel substituted 2,6-dinitroaniline compounds which are useful herbicides.

5 Claims, No Drawings

4-CYANO-2,6-DINITROANILINES

CROSS REFERENCE TO RELATED APPLICATIONS

This application is a continuation-in-part of Ser. No. 705,864 filed Jul. 16, 1976 and now abandoned, which is a continuation-in-part of Ser. No. 599,288 filed Jul. 25, 1975 and now abandoned, which is a division of Ser. No. 323,000 filed Jan. 12, 1973, now U.S. Pat. No. 3,920,742, 1975, which is a continuation-in-part of Ser. No. 262,807, filed Jun. 14, 1972, now abandoned, which in turn is a continuation-in-part of Ser. No. 174,938, filed Aug. 25, 1971, now abandoned.

This invention relates to certain novel substituted 2,6-dinitroaniline compounds. It further relates to certain novel preemergence herbicidal methods and compositions employing substituted 2,6-dinitroaniline compounds.

The novel 2,6-dinitroaniline compounds of the present invention may be represented by the following structural formula:

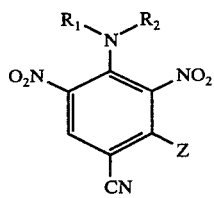

I wherein,

Z is alkyl $C_1$–$C_4$, alkenyl $C_2$–$C_4$ or mono-substituted alkyl $C_1$–$C_4$ where the substituent is halogen, alkoxy $C_1$–$C_4$ or —$NR_3$—$R_4$;

$R_1$ is hydrogen, alkyl $C_1$–$C_6$, alkenyl $C_2$–$C_6$ or alkynyl $C_2$–$C_6$;

$R_2$ is alkyl $C_2$–$C_7$ (straight, branched or cyclo), alkenyl $C_2$–$C_6$, alkynyl $C_2$–$C_6$ or mono-substituted alkyl $C_1$–$C_4$ where the substituent is halogen or alkoxy $C_1$–$C_4$;

$R_3$ and $R_4$ each are hydrogen or alkyl $C_1$–$C_4$; and when $R_1$ and $R_2$ are taken together they are piperidino, pyrrolidino or morpholino.

Illustrative lower alkyl substituents are methyl, ethyl, n-propyl, iso-propyl, n-butyl, t-butyl, n-pentyl, n-hexyl, 2-pentyl, 3-pentyl, sec-butyl, and the like.

Illustrative loweralkenyl substituents are ethenyl, 1-propenyl, 2-propenyl, 1-butenyl, 2-butenyl, 3-butenyl, 1-pentyl, 1-hexenyl, and the like.

Illustrative loweralkynyl substituents are ethynyl, 1-propynyl, 2-propynyl, 1-butynyl, 2-butynyl, 3-butynyl, 1-pentynyl, 1-hexynyl, and the like.

Illustrative cyclic hydrocarbons are cyclopropyl, cyclobutyl, cyclopentyl, and cyclohexyl groups.

Illustrative halogen substituents are fluoro, chloro, bromo and iodo groups.

The above-identified compounds are highly effective herbicidal agents and particularly efficacious are those represented by the following formula:

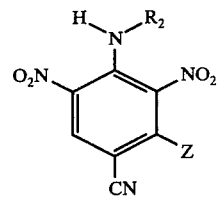

II wherein, $R_2$ is a secondary $C_3$–$C_5$ alkyl group free from quanternary carbon atoms and Z is $CH_3$ or —$CH_2OCH_3$.

These compounds represent a preferred class of compounds within the above-broader generic class and show a marked superiority in herbicidal performance.

The herbicidal methods of the present invention comprise application of a herbicidally effective amount of one or more compounds of Formula III below to the soil containing the seeds of undesirable plant species to be controlled.

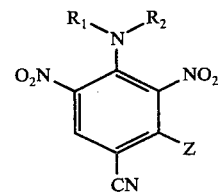

III wherein,

Z is alkyl $C_1$–$C_4$, alkenyl $C_2$–$C_4$ or mono-substituted alkyl $C_1$–$C_4$ where the substituent is halogen, alkoxy $C_1$–$C_4$ or —$NR_3R_4$;

$R_1$ is hydrogen, alkyl $C_1$–$C_6$, alkenyl $C_2$–$C_6$ or alkynyl $C_2$–$C_6$;

$R_2$ is alkyl $C_1$–$C_7$ (straight, branched or cyclo), alkenyl $C_2$–$C_6$, alkynyl $C_2$–$C_6$, or mono-substituted alkyl $C_1$–$C_4$ where the substituent is halogen or alkoxy $C_1$–$C_4$;

$R_3$ and $R_4$ each are hydrogen or alkyl $C_1$–$C_4$, and when $R_1$ and $R_2$ are taken together they are piperidino, pyrrolidino or morpholino.

Wherein an asymmetric carbon atom exists in the dinitroaniline compounds above, optical isomerism may exist. Accordingly, such compounds may be employed as separate antimers or in admixture, as in a racemic composition. Unless there is indication to the contrary by reference to such a compound, the unresolved composition is intended herein. Separation of antimers, where desired, may be effected by conventional resolution techniques. A convenient method relates to the introduction of an optically active substituent, such as a (-)-sec-butylamino group into the ring system, as by nucleophilic substitution, as exemplified below.

Preferably, application of these compounds, or active ingredients is made using the herbicidal compositions described below with conventional application methods.

The 2,6-dinitroaniline compounds can be prepared by reactions A or B, shown below:

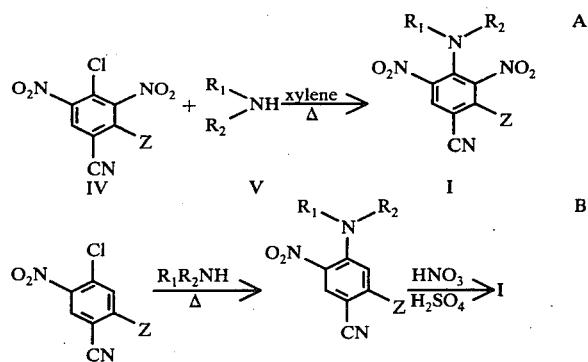

While chloro is a preferred substituent, and the discussion is in terms thereof other conventional equivalent substituents, such as, bromo or iodo are included herein. The displacement may be conducted with or without an organic solvent, such as toluene, benzene or preferably xylene. The reaction is carried out by heating the reactants, preferably between 50° and 150° C.

The compounds are prepared by reacting the appropriate 3,5-disubstituted-4-cyano-2,6-dinitrochlorobenzene with the appropriate amine.

o-Toluoyl chlorides may be prepared by reacting 3,5-dinitro-4-chloro-o-toluic acid with phosphorus pentachloride. The resulting o-toluoyl chloride is then treated with ammonia in cold acetone to yield the corresponding 3,5-dinitro-4-chloro-o-toluamide which is converted to the corresponding nitrile by reaction with phosphorus pentoxide or preferably with $POCl_3$.

The preemergence herbicidal compositions of the present invention are solid or liquid formulations comprising an effective amount of one or more of the 2,6-dinitroaniline compounds of Formula I, or preferably Formula II, and those compounds corresponding to Formula I wherein $R_2$ also represents methyl with a herbicidal adjuvant, i.e., an inert carrier or other conventional formulation aid.

Preparation of the compositions broadly involves admixing an effective amount of the herbicidal agent and adjuvant.

Use of the compositions broadly involves applications of an effective amount of said compounds or preferably said compositions to the soil containing seeds of the plants to be controlled.

Typical formulations include, for example, dusts, dust concentrates, wettable powders, granulars, and the like. Application by conventional methods and equipment is usually made at rates of from about ⅛ pound per acre to about 20 pounds per acre and preferably ¼ to 8 pounds per acre of active material.

Dusts are generally prepared by grinding together from about 1% to 15% by weight of the active material with from about 99% to 85% by weight of a solid diluent, such as an attaclay, kaolin, diatomaceous earth, fullers earth, talc, pumice or the like.

Dust concentrates are prepared in similar fashion to the dusts excepting that generally about 15% to about 95% by weight of active material is used.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of naphthalene sulfuric acid and anionic-nonionic blends, and from about 1% to 5% by weight of a surfactant, such as polyoxyethylene alcohols, acids, adducts, sorbitan fatty acid esters and sorbitol esters. Typical formulations by weight percent are given below.

TABLE I

| Typical Wettable Powder Formulations | |
|---|---|
| A | Ingredients |
| 25% | 4-cyano-3-methyl-2,6-dinitro-N,N-dipropyl-aniline |
| 65% | attaclay |
| 5% | sodium lignosulfonate |
| 5% | sodium N-methyl-N-oleoyl taurate |
| B | Ingredients |
| 33% | 4-cyano-3-methyl-2,6-dinitro-N,N-dipropyl-aniline |
| 59% | attaclay |
| 5% | sodium lignosulfonate |
| 3% | alkyl phenoxy polyoxyethylene ethanol |
| C | Ingredients |
| 40% | 4-cyano-3-methyl-2,6-dinitro-N,N-dipropyl-aniline |
| 50% | precipitated hydrated silicon dioxide (Hi Sil)[a] |
| 5% | sodium lignosulfonate |
| 3% | anionic-nonionic blend (MAL-77L)-[b] |
| 2% | wetting agent |

[a] By Pittsburgh Plant Glass Company
[b] By Wm. Cooper and Nephews

The wettable powder formulations are usually dispersed in water and applied as a liquid spray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

The practice and advantages of the present invention and preparation of the active ingredients used therein is further illustrated by the following examples which are not to be taken as being limitative thereof. Parts and percentages herein are by weight unless otherwise indicated.

EXAMPLE 1

Preparation of 3,5-Dinitro-4-chloro-o-toluoyl Chloride

Ten grams of 3,5-dinitro-4-chloro-o-toluic acid is warmed on a water bath with 9.2 grams of phosphorus pentachloride and 30 ml. of benzene. After the solids dissolve, the benzene is distilled and the phosphorus oxychloride is removed under reduced pressure. The desired product as a residual oil solidifies on chilling.

EXAMPLE 2

Preparation of 3,5-Dinitro-4-chloro-o-toluamide 3,5-Dinitro-4-chloro-o-toluoyl chloride is treated with two equivalents of ammonia in cold acetone. The mixture is poured into water and the desired product as a precipitated solid collected by filtration.

EXAMPLE 3

Preparation of 3,5-Dinitro-4-chloro-o-toluonitrile

A finely powdered mixture of 15.5 grams (0.051 mole) of 3,5-dinitro-4-chloro-o-toluamide is heated with 12 grams (0.084 mole) of phosphorus pentoxide for 15 minutes at 300° C. to 350° C. The resulting nitrile is distilled from the reaction flask. Recrystallization of the solidified product from methanol gives the desired product as an analytically pure material.

EXAMPLE 4 and 5

Preparation of 4-Cyano-3-methyl-2,6-dinitro-N,N-dipropylaniline

A mixture of 4.82 grams of 3,5-dinitro-4-chloro-o-toluonitrile and 3 grams of di-n-propylamine in 25 ml. of toluene is refluxed 8 hours. The cooled mixture is then washed with water, dilute acid, and finally water. The organic layer is separated and dried over MgSO$_4$. Removal of the drying agent by filtration and concentration of the filtrate in vacuo leaves a residual oil when crystallized gives the product with melting point 97° to 99° C.

N-sec-butyl-4-cyano-3-methyl-2,6-dinitroaniline is prepared by the above procedure substituting sec-butylamine for the di-n-propylamine. The desired product possessed a melting point of 102° to 103° C.

Examples 6–13 illustrate the preparation of the compound 4-cyano-N-(1-ethylpropyl)-α-methoxy-2,6-dinitro-m-toluidine.

EXAMPLE 6

Methyl-4-chloro-α-methoxy-o-toluate

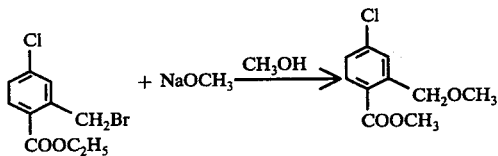

Ethyl α-Bromo-4-chloro-o-toluate (26.4 g.) is added to a solution (10°) of sodium methoxide (5.4 g.) in 110 ml. of methanol. When the addition is complete, the mixture is refluxed for two hours, then cooled and concentrated in vacuo. The oily residue is partioned between ether-water. The ether layer is separated and dried. Removal of the drying agent and concentration of the filtrate in vacuo leaves 17.3 g. of a white solid. A sample of the product recrystallized from methanol had mp 44°–45°.

EXAMPLE 7

Methyl 4-chloro-α-methoxy-5-nitro-o-toluate

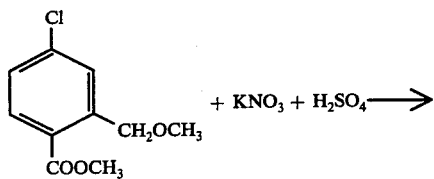

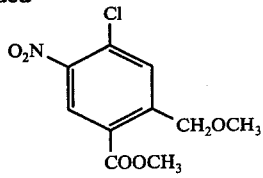

A sample of methyl 4-chloro-α-methoxy-o-toluate (10 g.) is added in small portions at 15°–20° to a solution of potassium nitrate (4.9 g.) in concentrated sulfuric acid. When the addition is complete, the mixture is stirred for 1 hour at 10°–15°, then poured onto ice and the precipitated solid (12.8 g.) collected by filtration. A sample of the damp product is recrystallized from 90% ethanol. After recrystallization, the solid mp is 77°–81°.

EXAMPLE 8

4-Chloro-α-methoxy-5-nitro-o-toluic acid

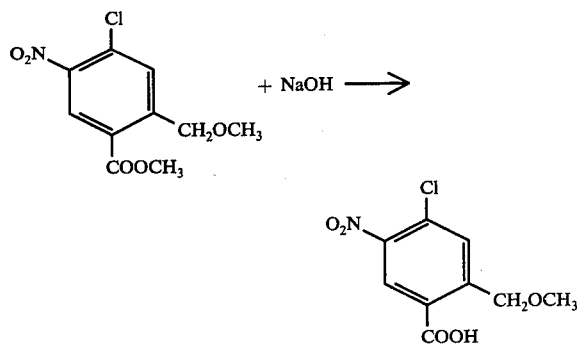

A slurry of methyl 4-chloro-α-methoxy-5-nitro-o-toluate (7.0 g.) in dilute sodium hydroxide (35 ml of 1N) is stirred about 30 hours. The yellow slurry is then diluted with 50 ml. of water resulting in a clear yellow solution. The solution is extracted with ether, then the aqueous layer is separated and acidified to give 5.7 g. of an off-white solid. A sample recrystallized from benzene has a mp 155°–157°.

EXAMPLE 9

4-Chloro-α-methoxy-5-nitro-o-toluoyl chloride

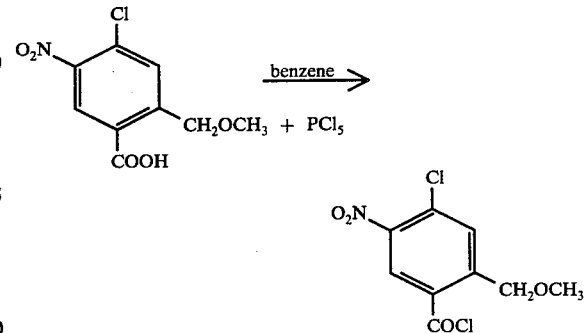

A mixture of 4-chloro-α-methoxy-5-nitro-o-toluic acid (3.6 g.) and phosphorus pentachloride (3.0 g.) in 120 ml of benzene is refluxed for thirty minutes. The mixture is then concentrated in vacuo and the residue boiled with 200 ml of hexane and filtered hot. The filtrate is partially concentrated and chilled to give 2.5 g. of white solid with mp 63°–65°.

EXAMPLE 10

4-Chloro-α-methoxy-5-nitro-o-toluamide

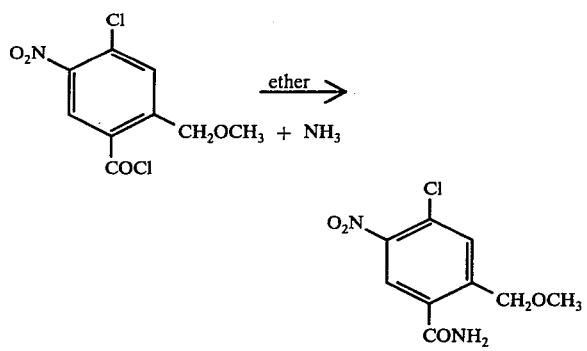

A sample of 4-chloro-α-methoxy-5-nitro-o-toluoyl chloride (1.5 g.) is added to 100 ml of ether saturated with ammonia. During the addition and for 15 minutes thereafter, the reaction temperature is kept below 20°. The precipitated solid is collected and washed well with water. The crude product (0.9) has an infrared compatible with the desired structure.

EXAMPLE 11

4-Chloro-α-methoxy-5-nitro-o-tolunitrile

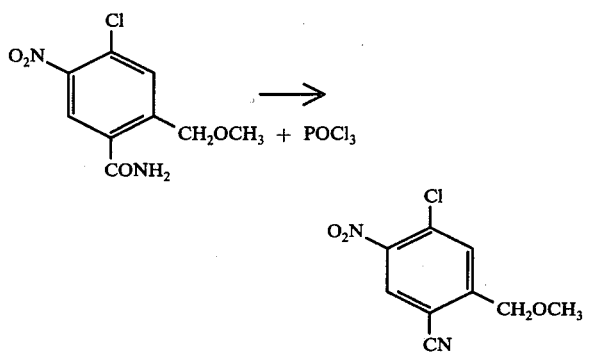

A sample of 4-chloro-α-methoxy-5-nitro-o-toluamide (0.8 g) is added to phosphorus oxychloride (10 ml) and the slurry gradually heated to reflux. After about 10 minutes at reflux, all the solid has dissolved giving a clear yellow solution. The solution is concentrated in vacuo and the crude residue is portioned between ether and water. The ether layer is separated and dried. Removal of the drying agent and concentration of the filtrate in vacuo leaves a crude solid (0.7 g.) with mp 57°–59°.

EXAMPLE 12

4-Cyano-N-(1-ethylpropyl)-α-methoxy-6-nitro-m-toluidine

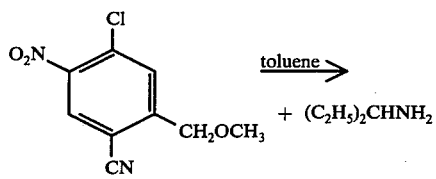

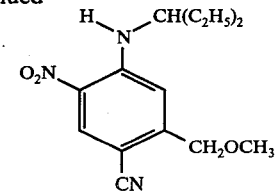

4-Chloro-α-methoxy-5-nitro-o-tolunitrile (0.7 g.) is added to 10 ml. of toluene and the resulting solution refluxed for 1 hour and then stirred overnight at room temperature. Since glc indicated the reaction was incomplete, it was refluxed an additional 30 minutes. The mixture is then cooled, washed with water, dilute hydrochloric acid, and finally saturated sodium chloride solution. The organic layer is separated and dried. Removal of the drying agent and concentration of the filtrate in vacuo leaves an oil which solidifies to a yellow solid (0.56). The solid is slurried with hexane and filtered to give a yellow solid with mp 45°–49°.

EXAMPLE 13

4-Cyano-N-(1-ethylpropyl)-α-methoxy-2,6-dinitro-m-toluidine

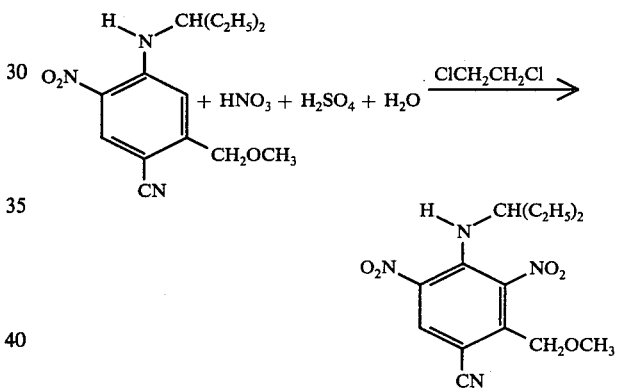

A sample of 4-cyano-N-(1-ethylpropyl)-α-methoxy-6-m-toluidine (0.4 g) in 10 ml. of 1,2-dichloroethane is treated with a nitrating mixture consisting of water (0.15 g), sulfuric acid (0.33 g.) and 70% nitric acid (0.4 g). When essentially no reaction is observed after several hours at room temperature, additional quantities of water (0.6g), sulfuric acid (1.6 g) and nitric acid (1.7 g) are added and stirring continued at 35° until tlc (benzene-silica gel) indicates no more starting material. After the usual work-up, 0.4 g. of dark oil is chromatographed on 10 g. of silica gel and developed using hexane and hexane-benzene mixtures. The major spot by tlc is isolated as a yellow solid (0.2 g) with mp 46°–49°. The IR and nmr are in agreement for the desired structure.

The remaining compounds of the invention are prepared in a similar manner.

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.25 to 4 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the tables below.

Rating System

| Rating System | % Difference in Growth from the Check* |
|---|---|
| 0 - no effect | 0 |
| 1 - possible effect | 1 – 10 |
| 2 - slight effect | 11 – 25 |
| 3 - moderate effect | 26 – 40 |
| 5 - definite injury | 41 – 60 |
| 6 - herbicidal effect | 61 – 75 |
| 7 - good herbicidal effect | 76 – 90 |
| 8 - approaching complete kill | 91 – 99 |
| 9 - complete kill | 100 |
| 4 - abnormal growth, i.e., a definite physiological malformation but with an over-all effect less than a 5 on the rating scale. | |

*Based on visual determination of stand, size, vigor, chlorosis, growth malformation and over-all plant appearance.

PLANT ABBREVIATIONS

CR — Crabgrass
VEL — Velvet Leaf
PI — Pigweed
LA — Lambsquarters
COR — Corn
WO — Wild oats
SE — Sesbania
MU — Mustard
BA — Barnyard grass
FOX — Green foxtail
MG — Annual Morning-glory
COT — Cotton
SB — Sugarbeets
SOY — Soybean
TW — Teaweed

TABLE II
Preemergence Herbicidal Evaluation of
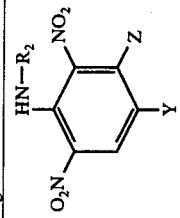
| Structure | | | Rate | Plant Species | | | | | | | | | | | | | | |
|---|---|---|---|---|---|---|---|---|---|---|---|---|---|---|---|---|---|---|
| R₂ | Z | Y | lb/Acre | SE | MU | PI | RG | MG | TW | VL | BA | CR | GF | WO | CN | CO | SY | SB | RI |
| CH(CH₃)C₂H₅ | CH₃ | CN | 10.0 | | 9 | 9 | 5 | 8 | 8 | 8 | 9 | 9 | 9 | 9 | | | | | |
| | | | 4.0 | | | 8 | | 3 | | 7 | 9 | 9 | *9 | 3 | 15* | *0 | *0 | *5 | |
| | | | 2.0 | | | *7 | | *0 | 5 | 6 | *8 | 8.7* | *0 | *0 | *1 | 4.5* | | | |
| | | | 1.0 | | | 6.5* | | *0 | | *8 | *9 | *8 | 7.3* | *1 | | | | | |
| | | | 0.50 | | | 3.5* | | *0 | | | 7.3* | *8 | *6 | | | | | | |
| | | | 0.25 | | | *0 | | *0 | | *0 | 5.7* | 7.3* | *6 | | | | | | |
| | | | 0.13 | *8 | *8 | | | | | | *3 | *8 | *6 | | | | | | |
| *Average of 2 to 3 Tests | | | 10.0 | | | *9 | *9 | *9 | *8 | *8 | *9 | *9 | *9 | *8 | *0 | *0 | *0 | 0.5* | |
| | | | 2.0 | | 7 | 7 | | 3 | 7 | 7 | *9 | *9 | *9 | 1 | 0 | 0 | 0 | 0 | |
| *Average of two Tests | | | 1.0 | 3 | 0 | 3 | 0 | 0 | 6 | 2 | *7.5 | *9 | *9 | 0 | 0 | | | | |
| CH(C₂H₅)₂ | CH₃ | CN | 0.50 | 0 | 2 | 2 | 0 | 0 | 2 | 0 | *7 | *8 | *8 | 0 | | | | | |
| | | | 0.25 | 0 | | *0 | 0 | *0 | 0 | *0 | *5.5 | *7 | *6 | | | | | | |
| | | | 0.13 | *0 | *0 | *0 | 0 | *0 | *0 | *3 | *1 | *0 | | | | | | | |
| | | | 0.06 | *0 | 7 | *0 | 0 | *0 | *0 | *3 | *3 | *9 | | | | | | | |
| | | | 0.03 | 0 | 0 | 0 | 0 | 0 | 0 | 9 | 9 | 9 | | 0 | 0 | 0 | 0 | 0 | 0 |
| CH(C₂H₅)₂ | CH₂OCH₃ | CN | 1.0 | 0 | 0 | 0 | 0 | 0 | 0 | 0 | 8 | 9 | 8 | | 0 | 0 | 0 | 6 | 0 |
| | | | 0.5 | 0 | 0 | 0 | 0 | 0 | 0 | 0 | 2 | 9 | 6 | | 0 | 0 | 0 | | 0 |
| | | | 0.25 | 0 | 0 | 0 | 0 | 0 | 0 | 0 | 0 | 9 | 0 | | 0 | 0 | 0 | | 0 |
| | | | 0.13 | 0 | 0 | 0 | 0 | 0 | 0 | 0 | 0 | 2 | 0 | 7 | 0 | 0 | 0 | | 0 |
| | | | 0.06 | 8 | 8 | 9 | 9 | 9 | 8 | 8 | 9 | 9 | 9 | | | | | | |
| CH(CH₃)C₃H₇-n | CH₃ | CN | 10.0 | | | 9 | | | | | 9 | 9 | 9 | | | | | | |
| | | | 2.0 | | | 9 | | | | | 9 | 9 | 9 | | | | | | |
| | | | 1.0 | | | | | | | | 9 | 9 | 9 | | | | | | |
| | | | 0.50 | | | | | | | | 8 | 9 | 8 | | | | | | |
| | | | 0.25 | | | | | | | | 7 | 9 | 2 | | | | | | |
| | | | 0.13 | | | | | | | | | | | | | | | | |

We claim:
1. A compound of the formula:
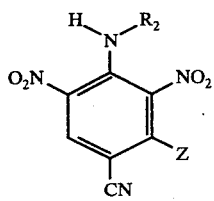
wherein
R₂ is secondary alkyl C₃–C₅ groups free from quaternary carbon atoms and
Z is CH₃ or —CH₂OCH₃.
2. A compound according to claim 1 of the formula:
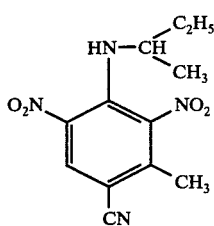
3. A compound according to claim 1 of the formula:
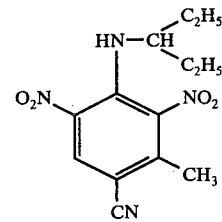
4. A compound according to claim 1 of the formula:
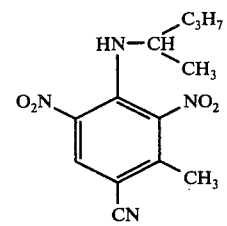
5. A compound according to claim 1 of the formula:
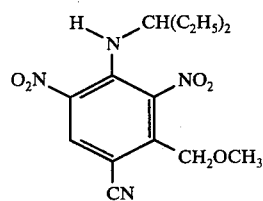
* * * * *